United States Patent
Kodama et al.

(10) Patent No.: US 7,390,915 B1
(45) Date of Patent: Jun. 24, 2008

(54) PHOSPHINE TRANSITION METAL COMPLEX HAVING FERROCENE SKELETON, PROCESS FOR MAKING THE SAME, AND ANTI-CANCER AGENT

(75) Inventors: Hiroaki Kodama, Saga (JP); Keisuke Ohto, Saga (JP); Nobuhiko Oohara, Tokyo (JP); Kazuhiro Nakatsui, Tokyo (JP); Yoshirou Kaneda, Tokyo (JP)

(73) Assignee: Nippon Chemical Industrial Co., Ltd, Tokyo (JP)

( * ) Notice: Subject to any disclaimer, the term of this patent is extended or adjusted under 35 U.S.C. 154(b) by 0 days.

(21) Appl. No.: 11/841,155

(22) Filed: Aug. 20, 2007

(51) Int. Cl.
*C07K 19/00* (2006.01)
*A61K 31/28* (2006.01)

(52) U.S. Cl. .................. 556/14; 556/143; 514/492

(58) Field of Classification Search .............. 556/14, 556/143; 514/492
See application file for complete search history.

(56) References Cited

U.S. PATENT DOCUMENTS

2006/0106100 A1* 5/2006 Caires et al. ............... 514/492

OTHER PUBLICATIONS

Lopez et al., Angewandte Chemie International Edition, vol. 44, No. 18, pp. 2752-2756 (2005).*
Mun et al., Organic Letters, vol. 8, No. 21, pp. 4887-4889 (2006).*
Gambs et al., Helvetica Chimica Acta, vol. 84, No. 10, pp. 3105-3126 (2001).*

* cited by examiner

*Primary Examiner*—Porfirio Nazario Gonzale
(74) *Attorney, Agent, or Firm*—Westerman, Hattori, Daniels & Adrian, LLP.

(57) ABSTRACT

An anti-cancer agent contains a phosphine transition metal complex having a ferrocene skeleton, the complex being represented by general formula (3) below:

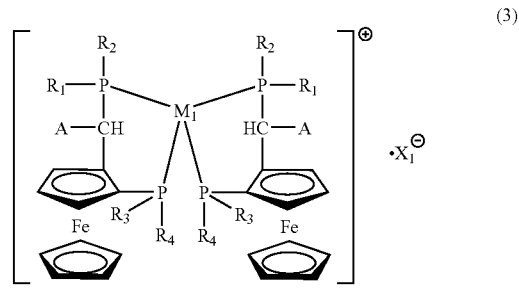

(wherein $R_1$, $R_2$, $R_3$, and $R_4$ each represent a linear or branched alkyl group, a cycloalkyl group, an alkoxy group, an aryl group, or an aralkyl group; A represents a linear or branched alkyl group, a phenyl group, or a hydrogen atom; $M_1$ represents a transition metal atom selected from the group consisting of gold, copper, platinum, and silver; and $X_1$ represents an anion).

10 Claims, No Drawings

PHOSPHINE TRANSITION METAL COMPLEX HAVING FERROCENE SKELETON, PROCESS FOR MAKING THE SAME, AND ANTI-CANCER AGENT

BACKGROUND OF THE INVENTION

1. Field of the Invention

The present invention relates to a novel phosphine transition metal complex having a ferrocene skeleton, a process for making the complex, and an anti-cancer agent containing the complex.

2. Description of the Related Art

It is widely known that cisplatin has excellent anti-tumor activity against cancerous cells. Cisplatin is currently the mainstream of anti-cancer agents. It is also known that some types of phosphine transition metal complexes including 1,2-bis(diphenylphosphino)ethane have anti-cancer activity comparable to that of cisplatin (e.g., refer to PCT Japanese Translation Patent Publication No. 10-509957 ('957 document) and Japanese Unexamined Patent Application Publication No. 61-10594 ('594 document)).

The aforementioned patent documents propose a phosphine transition metal complex represented by general formula (6) below.

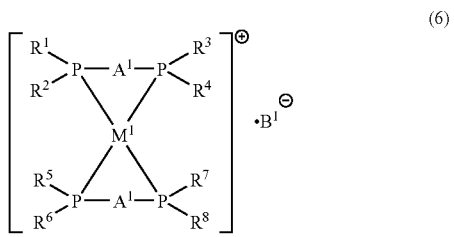

'957 document provides a phosphine transition metal complex represented by general formula (6) wherein $R^1$ to $R^8$ may be the same or different and each represent a group selected from phenyl, substituted phenyl, 4-pyridyl, 3-pyridyl, and 2-pyridyl, $A^1$ represents $-(CH_2)_n-$ or cis-CH=CH—, $M^1$ represents gold, silver, or copper; and $B^1$ represents a halogen atom such as chlorine. '594 document provides a phosphine transition metal complex represented by general formula (6) wherein $R^1$ to $R^8$ represent the same group selected from a phenyl group, an ethyl group, or a mono-substituted phenyl group, $A^1$ represents $-(CH_2)_n-$ or cis-CH=CH—, $M^1$ represents gold, silver, or copper; and $B^1$ represents a halogen atom such as chlorine, and a phosphine transition metal complex wherein $B^1$ represents halogen, $PF_6$, or $NO_3$.

In general, it is known that anti-cancer activity and anti-cancer spectrum of a compound depend upon the chemical structure of the compound and that the efficacy of the compound differs from person to person. For example, even taxol, which is considered as the best anti-cancer agent, has an efficacy of only about 30%. Development of various novel anti-cancer agents with different chemical structures is desired.

The present inventors have conducted extensive investigations on novel phosphine transition metal complexes having anti-cancer activity and found that a phosphine transition metal complex produced by reacting a phosphine derivative having a particular structure with a transition metal salt of gold, copper, platinum, or silver has excellent anti-cancer activity. Thus, the present inventors have made the present invention on the basis of such findings.

SUMMARY OF THE INVENTION

An object of the present invention is to provide a phosphine transition metal complex having excellent anti-cancer activity, a process for making the phosphine transition metal complex, and an anti-cancer agent containing the phosphine transition metal complex.

A first aspect of the present invention provides a phosphine transition metal complex having a ferrocene skeleton, the complex containing at least two phosphine derivatives represented by general formula (1) or general formula (2) as ligands and a transition metal atom selected from the group consisting of gold, copper, platinum, and silver:

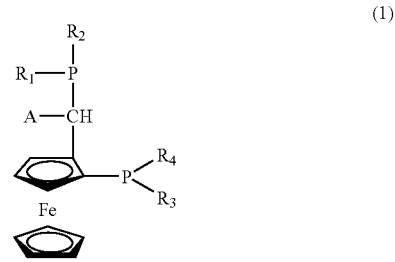

(wherein $R_1$, $R_2$, $R_3$, and $R_4$ each represent a linear or branched alkyl group, a cycloalkyl group, an alkoxy group, an aryl group, or an aralkyl group; and A represents a linear or branched alkyl group, a phenyl group, or a hydrogen atom),

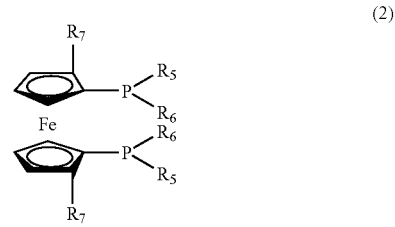

(wherein $R_5$ and $R_6$ each represent a linear or branched alkyl group, a cycloalkyl group, an alkoxy group, an aryl group, or an aralkyl group, and $R_7$ represents a monovalent organic group).

A second aspect of the present invention provides a process for making the phosphine transition metal complex having the ferrocene skeleton according to the first aspect of the invention, the method including reacting a phosphine derivative represented by general formula (1) or (2) above with a transition metal salt of gold, copper, platinum, or silver.

A third aspect of the present invention provides an anti-cancer agent containing the phosphine transition metal complex having the ferrocene skeleton according to the first aspect of the present invention.

The phosphine transition metal complex having the ferrocene skeleton according to the present invention is a compound having superior anti-cancer activity. Moreover, the process of the present invention achieves industrial advantages in producing the phosphine transition metal complex.

DESCRIPTION OF THE PREFERRED EMBODIMENTS

The present invention will now be described in detail by way of preferred embodiments.

A phosphine transition metal complex of the present invention having a ferrocene skeleton is produced by reacting a phosphine derivative represented by general formula (1) or (2) below with a transition metal salt of gold, copper, platinum, or silver:

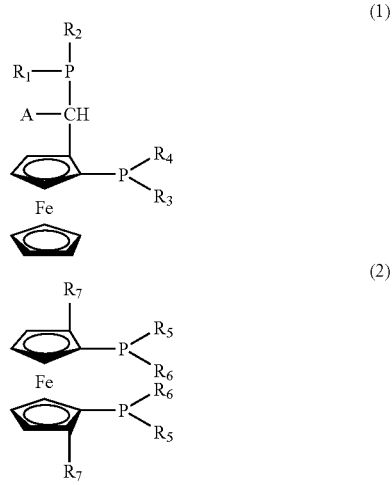

The resulting phosphine transition metal complex contains at least two phosphine derivatives represented by general formula (1) or (2) as the ligands and has a transition metal atom selected from gold, copper, platinum, and silver.

In general formula (1), $R_1$, $R_2$, $R_3$, and $R_4$ each represent a linear or branched alkyl group, a cycloalkyl group, an alkoxy group, an aryl group, or an aralkyl group. Examples of the alkyl group include linear or branched $C_1$-$C_{18}$ alkyl groups such as methyl, ethyl, n-propyl, iso-butyl, tert-butyl, n-hexyl, iso-hexyl, n-heptyl, n-octyl, iso-octyl, n-dodecyl, iso-dodecyl, n-octadecyl, and iso-octadecyl groups. Of these, $C_1$-$C_5$ alkyl groups are particularly preferred. Examples of the cycloalkyl group include cyclopentyl and cyclohexyl groups. Examples of the aryl group include phenyl, tolyl, xylyl, and naphthyl groups. Examples of the aralkyl group include benzyl and phenethyl groups. Of these, $R_1$, $R_2$, $R_3$, and $R_4$ in the formula each preferably represent a group selected from cyclohexyl and phenyl groups. $R_1$, $R_2$, $R_3$, and $R_4$ may be the same or different; however, particularly preferably, $R_1$ and $R_2$ are the same group and $R_3$ and $R_4$ are the same group.

A in general formula (1) represents a linear or branched alkyl group, a phenyl group, or a hydrogen atom. Examples of the alkyl group include linear or branched $C_1$-$C_{18}$ alkyl groups such as methyl, ethyl, n-propyl, iso-butyl, tert-butyl, n-hexyl, iso-hexyl, n-heptyl, n-octyl, iso-octyl, n-dodecyl, iso-dodecyl, n-octadecyl, and iso-octadecyl groups. The alkyl group is preferably a linear or branched $C_1$-$C_5$ alkyl group. A in the formula is particularly preferably a methyl group among these groups.

$R_5$ and $R_6$ in general formula (2) each represent a linear or branched alkyl group, a cycloalkyl group, an alkoxy group, an aryl group, or an aralkyl group. Examples of the alkyl group include linear or branched $C_1$-$C_{18}$ alkyl groups such as methyl, ethyl, n-propyl, iso-butyl, tert-butyl, n-hexyl, iso-hexyl, n-heptyl, n-octyl, iso-octyl, n-dodecyl, iso-dodecyl, n-octadecyl, and iso-octadecyl groups. The alkyl group is particularly preferably a $C_1$-$C_5$ alkyl group. Examples of the alkoxy group include methoxy, ethoxy, isopropoxy, and phenoxy groups. Examples of the cycloalkyl group include cyclopentyl and cyclohexyl groups. Examples of the aryl group include phenyl, tolyl, xylyl, and naphthyl. Examples of the aralkyl group include benzyl and phenethyl. $R^5$ and $R^6$ in the formula are particularly preferably phenyl among these groups. $R_5$ and $R_6$ may represent the same group or different groups.

$R_7$ in general formula (2) is a monovalent organic group. The monovalent organic group is not particularly limited. Examples of the monovalent organic group include substituted or unsubstituted oxazoline groups, linear or branched $C_1$-$C_5$ alkyl groups, linear or branched $C_1$-$C_5$ alkoxy groups, a carboxyl group, a carboxylic ester group, and a group represented by general formula, $-C(B_1)N(B_2)(B_3)$ (wherein $B_1$, $B_2$, and $B_3$ each represent a linear or branched $C_1$-$C_5$ alkyl group or a phenyl group). $R_7$ in the formula is preferably a substituted or unsubstituted oxazoline group, a linear or branched $C_1$-$C_5$ alkyl group, a carboxyl group, or a carboxylic ester group among these groups. Examples of the substituent of the oxazoline group include a phenyl group, linear or branched $C_1$-$C_6$ alkyl groups, $C_1$-$C_6$ alkoxy groups, and a halogen atom. Examples of the carboxylic ester group include a group represented by $-COOB_4$, wherein $B_4$ represents a linear or branched $C_1$-$C_8$ alkyl group or a group represented by general formula (2-1) below:

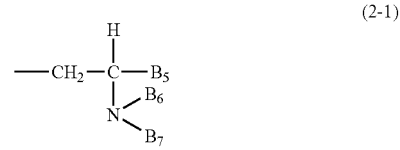

(wherein $B_5$ represents a linear or branched $C_1$-$C_5$ alkyl group or a hydrogen atom; and $B_6$ and $B_7$ each represent a linear or branched $C_1$-$C_5$ alkyl group, an acetyl group, or a hydrogen atom).

Examples of the transition metal salt of gold, copper, platinum, or silver include halides, nitrates, perchlorates, tetrafluoroborates, and hexafluorophosphates of these transition metals. Examples of the preferable transition metal salts of gold include dichloroaurate(I), gold(I) chloride, and tetrabutylammonium dichloroaurate(I) (refer to Experimental Chemistry Course (*Jikken Kagaku Koza*) 21, 5th Edition, edited by the Chemical Society of Japan, published by Maruzen, publishing date: Mar. 30, 2004, pp. 366-380, and Aust. J. Chemm., 1997, 50, 775-778). Examples of the preferable transition metal salts of copper include copper(I) chloride, copper(I) bromide, and copper(I) iodide (Experimental Chemistry Course (*Jikken Kagaku Koza*) 21, 5th Edition, edited by the Chemical Society of Japan, published by Maruzen, publishing date: Mar. 30, 2004, pp. 349-361). Examples of the preferable transition metal salts of platinum include platinum(II) chloride, sodium tetrachloroplatinate (II), and potassium tetrachloroplatinate(II) (Experimental Chemistry Course (*Jikken Kagaku Koza*) 21, 5th Edition, edited by the Chemical Society of Japan, published by Maruzen, publishing date: Mar. 30, 2004, pp. 327-348). Examples of the preferable transition metal salts of silver include silver(I) chloride, silver(I) bromide, and silver(I) iodide (Experimental Chemistry Course (*Jikken Kagaku*

*Koza*) 21, 5th Edition, edited by the Chemical Society of Japan, published by Maruzen, publishing date: Mar. 30, 2004, pp. 361-366). The transition metal salts described above may be hydrides or anhydrides.

In the present invention, preferable phosphine transition metal complexes having the ferrocene skeleton are phosphine transition metal complexes represented by following general formulae (3) to (5):

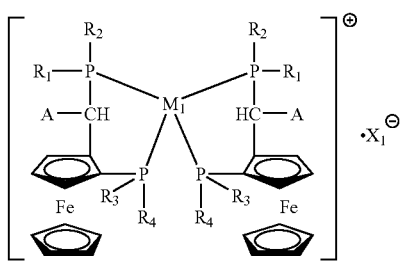
(3)

(wherein $R_1$, $R_2$, $R_3$, $R_4$, and A are the same as above, $M_1$ represents a transition metal atom selected from the group consisting of gold, copper, platinum, and silver, and $X_1$ represents an anion);

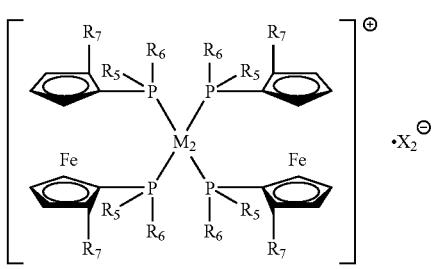
(4)

(wherein $R_5$, $R_6$, and $R_7$ are the same as above, $M_2$ represents a transition metal atom selected from the group consisting of gold, copper, platinum, and silver, and $X_2$ represents an anion); and

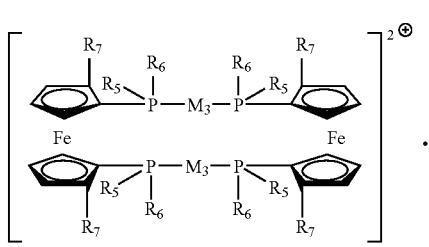
(5)

(wherein $R_5$, $R_6$, and $R_7$ are the same as above, $M_3$ represents a transition metal atom selected from the group consisting of gold, copper, platinum, and silver, and $X_3$ represents an anion).

$M_1$, $M_2$, and $M_3$ in general formulae (3) to (5) above each represent a transition metal atom selected from the group consisting of gold, copper, platinum, and silver, and most preferably a gold atom.

$X_1$, $X_2$, and $X_3$ in general formulae (3) to (5) each represent an anion species, for example, chlorine, iodine, bromine, boron tetrafluoride, hexafluorophosphoric acid, perchloric acid, or the like. Among these, halogen atoms such as chlorine, bromine, and iodine are particularly preferred.

Of the phosphine transition metal complexes represented by general formulae (3) to (5), particularly preferred compounds are a phosphine transition metal complex represented by general formula (3) where $R_1$, $R_2$, $R_3$, and $R_4$ each represent a group selected from the group consisting of phenyl and cycloalkyl; a phosphine transition metal complex represented by general formula (4) where $R_7$ selected from the group consisting of a linear or branched $C_1$-$C_5$ alkyl group, a carboxyl group, and a carboxylic ester group; and a phosphine transition metal complex represented by general formula (5) where $R_7$ represents a substituted or unsubstituted oxazoline group.

The phosphine transition metal complex having the ferrocene skeleton according to the present invention may be an optically active substance.

The phosphine transition metal complex having the ferrocene skeleton according to the present invention is synthesized by reacting a phosphine derivative represented by general formula (1) or (2) with a transition metal salt of gold, copper, platinum, or silver. For example, a phosphine derivative represented by general formula (1) is reacted with a transition metal salt of gold, copper, platinum, or silver to yield a phosphine transition metal complex represented by general formula (3) having a ferrocene skeleton. A phosphine derivative represented by general formula (2) is reacted with a transition metal salt of gold, copper, platinum, or silver to yield a phosphine transition metal complex represented by general formula (4) or (5) having a ferrocene skeleton.

For example, a phosphine derivative represented by general formula (3) can be obtained by reacting a phosphine derivative represented by general formula (1) with a transition metal salt of gold, copper, platinum, or silver under the following conditions: The phosphine derivative represented by general formula (1) in an amount 1 to 5 and preferably 1.8 to 2.2 times the amount of the transition metal salt in terms of mole is reacted with the transition metal salt at a temperature of −20° C. to 60° C., preferably 0° C. to 25° C. for 0.5 to 48 hours, preferably 1 to 3 hours. Usually, the reaction is conducted in a solvent such as acetone, acetonitrile, methanol, ethanol, chloroform, or tetrahydrofuran to produce the phosphine derivative represented by general formula (3).

A phosphine transition metal complex represented by general formula (4) or (5) can be selectively obtained by appropriately selecting the group $R_7$ in general formula (2) for the reaction between the phosphine transition metal complex represented by general formula (2) and a transition metal salt of gold, copper, platinum, or silver. For example, in order to obtain a preferable compound of the phosphine transition metal complex represented by general formula (4), a phosphine derivative represented by general formula (2) where $R_7$ represents a group selected from the group consisting of a linear or branched $C_1$-$C_5$ alkyl group, a carboxyl group, and a carboxylic ester group may be used. The reaction conditions are as follows: A phosphine derivative represented by general formula (2) in an amount 1 to 5 and preferably 1.5 to 2.2 times the amount of the transition metal salt in terms of mole is reacted with the transition metal salt at a reaction temperature of −20° C. to 60° C., preferably 0° C. to 25° C. for 0.5 to 48 hours, preferably 1 to 3 hours. The reaction is usually conducted in a solvent such as acetone, acetonitrile, methanol, ethanol, chloroform, tetrahydrofuran, or the like.

In order to obtain a preferable compound of the phosphine transition metal complex represented by general formula (5), a phosphine derivative represented by general formula (2) where $R_7$ represents the aforementioned substituted or unsubstituted oxazoline group may be used. The reaction conditions are as follows: A phosphine derivative represented by general formula (2) in an amount 0.4 to 3, preferably 0.6 to 1.5 times the amount of the transition metal salt in terms of mole is reacted with the transition metal salt at a reaction temperature of −20° C. to 60° C., preferably 0° C. to 25° C. for 0.5 to 48 hours, preferably 1 to 3 hours. The reaction is usually conducted in a solvent such as acetone, acetonitrile, methanol, ethanol, chloroform, tetrahydrofuran, or the like.

After completion of the reaction, purification by a known method may be conducted to produce products.

Alternatively, in the present invention, a phosphine transition metal complex represented by general formula (3), (4), or (5) having a ferrocene skeleton in which $X_1$, $X_2$, or $X_3$ in the formula is a halogen atom may be synthesized and then be reacted with a desirable inorganic acid, organic acid, or alkali metal salt of an organic or inorganic acid in a solvent to convert $X_1$, $X_2$, or $X_3$ to another anion (refer to Japanese Unexamined Patent Application Publication Nos. 10-147590, 10-114782, and 61-10594).

Note that the phosphine derivative represented by general formula (1), which is the starting material used in the present invention, is a known compound and can be produced by reacting a compound (7) or (9) with a phosphine compound (8) according to reaction scheme (1) below:

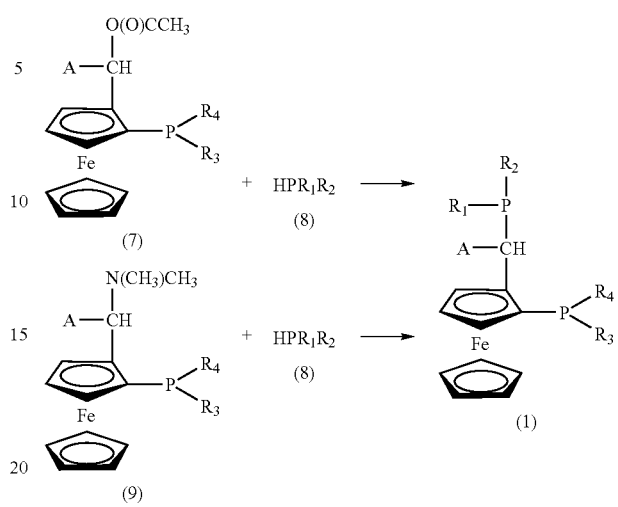

Reaction Scheme (1)

(wherein $R_1$, $R_2$, $R_3$, $R_4$, and A are the same as above)

The phosphine derivative represented by general formula (2), which is the starting material used in the present invention, is also a known compound. Phosphine derivatives (compounds (2a) to (2h)) corresponding to the phosphine derivative represented by general formula (2) can be synthesized through reaction scheme (2) or (3) (refer to Journal of the Society of Synthetic Organic Chemistry, Japan, vol. 61, No. 3, 2003, pp. 211-225, Japanese Unexamined Patent Application Publication Nos. 2-62886, 9-59290, and 10-45787). For example, as described in Japanese Unexamined Patent Application Publication No. 2000-256384, a phosphine derivative corresponding to one represented by general formula (2) can be easily synthesized by synthesizing a borane complex such as 1,1-bis(dialkylphosphino)ferrocene borane and then removing borane.

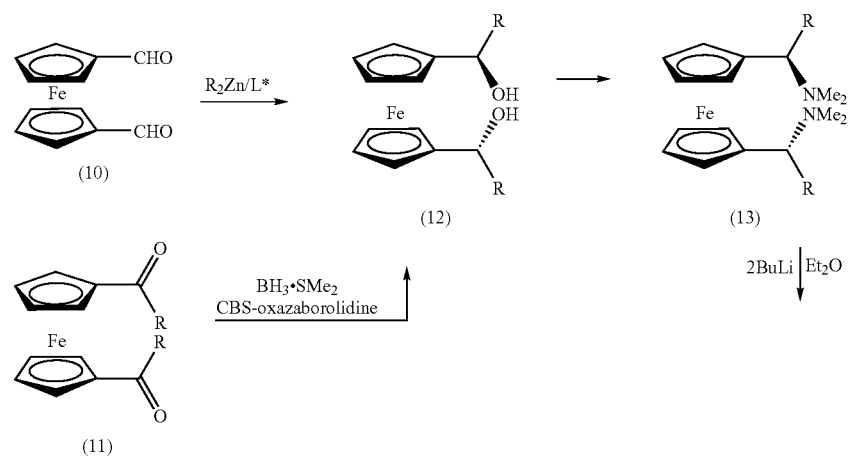

Reaction Scheme (2)

-continued
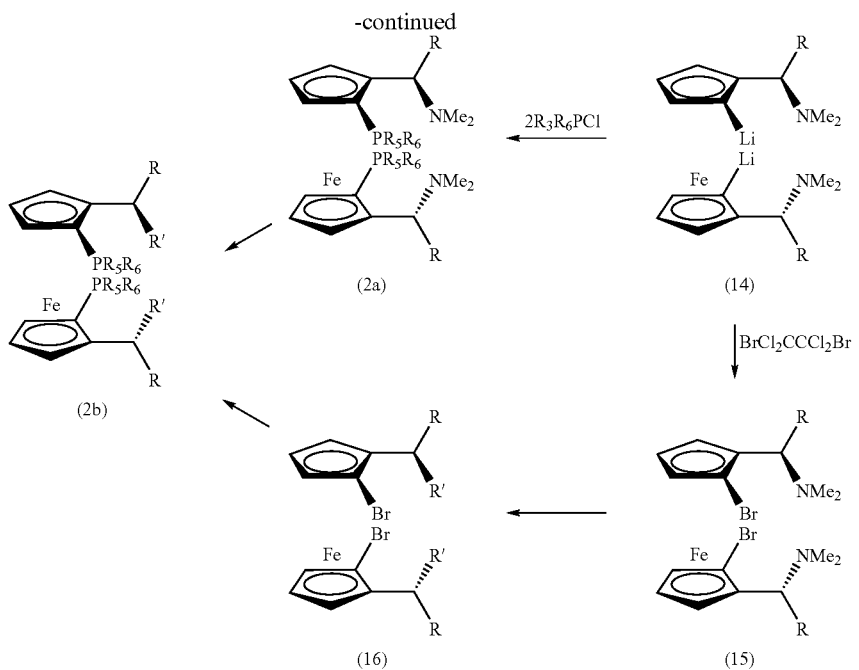
(wherein $R_5$ and $R_6$ are the same as above, and R and R' each represent a suitable monovalent organic group or a hydrogen atom).
Reaction Scheme (3)
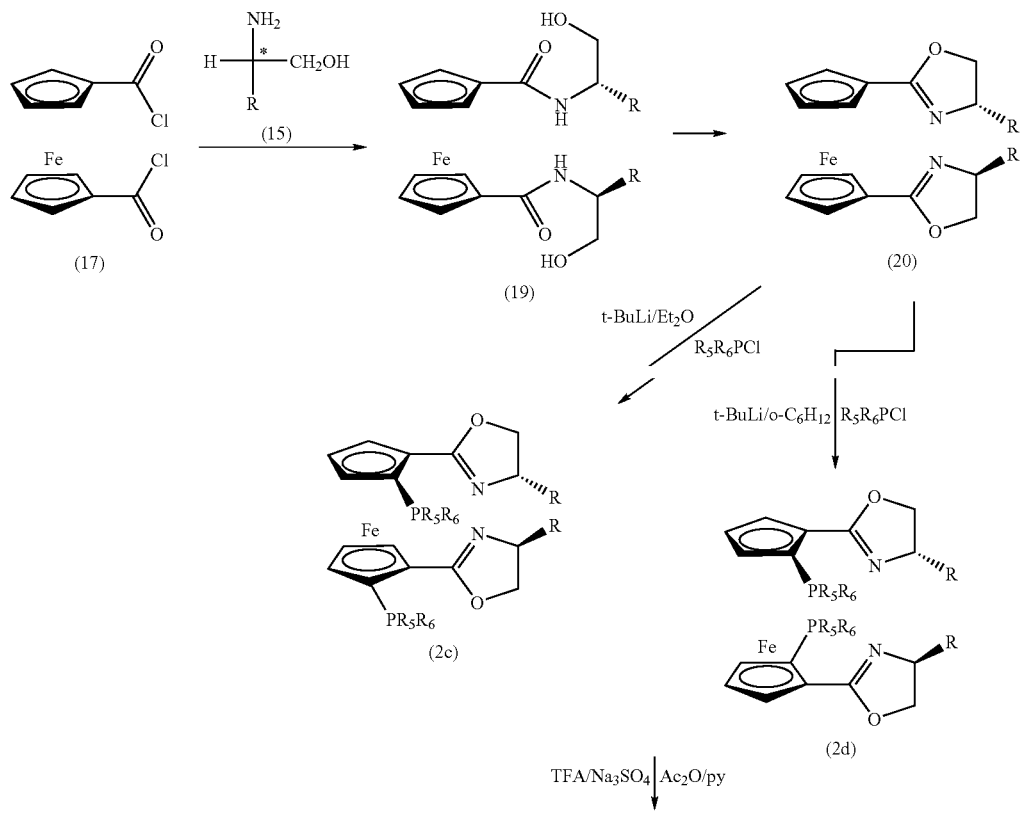

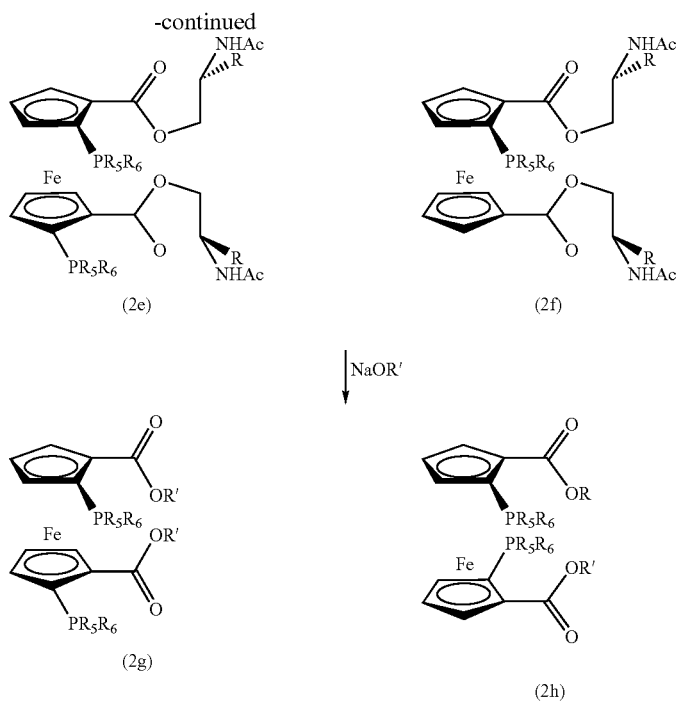

(wherein $R_5$ and $R_6$ are the same as above, R and R' each represent a suitable monovalent organic group or a hydrogen atom, and the asterisked carbon indicates the asymmetric center).

The phosphine transition metal complex of the present invention has remarkable anti-cancer activity as described below and can be used as an anti-cancer agent.

That is, the anti-cancer agent of the present invention contains at least one type of the phosphine transition metal complex having a ferrocene skeleton.

The type of cancer to which the anti-cancer agent of the present invention can be applied is not particularly limited. For example, the anti-cancer agent of the present invention can be applied to malignant melanoma, malignant lymphoma, digestive cancer, lung cancer, esophageal cancer, gastric cancer, large intestinal cancer, rectum cancer, colon cancer, ureteral tumor, gallbladder cancer, bile duct cancer, biliary tract cancer, breast cancer, liver cancer, pancreas cancer, testis tumor, maxillary cancer, lingual cancer, lip cancer, mouth cancer, pharyngeal cancer, laryngeal cancer, ovarian cancer, cervix cancer, prostate cancer, thyroid cancer, brain tumor, Kaposi's sarcoma, vascular neoplasm, leukemia, polycythemia vera, neuroblastoma, retinoblastoma, myeloma, bladder tumor, sarcoma, osteosarcoma, myosarcoma, skin cancer, basal cell cancer, skin appendage cancer, metastatic skin cancer, and cutaneous melanoma. Furthermore, the anti-cancer agent of the present invention can be applied to not only malignant tumor but also benign tumor and can also be used to suppress metastasis of cancer. It is also useful as a postoperative metastasis-suppressive agent.

The anti-cancer agent of the present invention may be administered to humans and animals in a variety of forms. The anti-cancer agent can be administered orally or non-orally, for example, through intravenous injection, intramuscular injection, subcutaneous injection, intracutaneous injection, intrarectal administration, and transmucosal administration. Examples of the forms of preparation suitable for oral administration include tablets, pills, granules, powder, capsules, liquid, suspension, emulsion, and syrup. Examples of the medicinal composition suitable for non-oral administration include injectable solution, intravenous drip, nasal drop, air spray, inhalant, suppository, and percutaneous therapies such as ointment, cream, powder liniment, liquid liniment, and transdermal patch. The anti-cancer agent of the present invention may also be used as a pellet for subcutaneous implant or a sustained-release preparation formed by a known technique.

A doctor may select the form of administration and the form of preparation preferable for a patient among the above-described examples according to the age, sex, constitution, symptom, timing of treatment, and the like of the patient.

In order to form a solid preparation of the agent of the present invention such as pills, powder drug, fine powder drug, or granular drug, the phosphine transition metal complex described above may be mixed adequate additives, e.g., an excipient such as lactose, saccharose, D-mannitol, cornstarch, synthetic or natural gum, and crystalline cellulose; a binder such as starch, hydroxypropylcellulose, hydroxypropylmethylcellulose, gum arabic, gelatin, and polyvinylpyrrolidone; a disintegrant such as carboxymethylcellulose calcium, carboxymethylcellulose sodium, starch, cornstarch, and sodium alginate; a gloss agent such as talc, magnesium stearate, and sodium stearate; a filler or diluent such as calcium carbonate, sodium carbonate, calcium phosphate, and sodium phosphate. If necessary, the tablets and the like may be covered with a sugarcoat, gelatin, enteric coat, film-coat, or the like by using a coating agent such as hydroxypropylmethylcellulose, sucrose, polyethylene glycol, titanium oxide, or the like.

In order to produce a liquid preparation of the agent of the present invention such as injectable solution, eye-drop, nasal drop, inhalant, air spray, lotion, syrup, liquid agent, suspension, or emulsion, the phosphine transition metal complex described above is dissolved in an adequate buffer such as purified water or a phosphate buffer, a physiological saline such as normal saline solution, Ringer's solution, or Locke's solution, a vegetable oil such as cacao butter, sesame oil, or olive oil, a mineral oil, a higher alcohol, a higher fatty acid, or an organic solvent such as ethanol, and then mixed with adequate additives, if necessary, such as an emulsifier such as cholesterol, a suspending agent such as gum arabic, a dispersion auxiliary, an infiltration agent, a surfactant such as a polyoxyethylene-hydrogenated castor oil-based agent and a polyethylene glycol-based agent, a solubilizing agent such as sodium phosphate, a stabilizer such as sugar, sugar alcohol, and albumin, a preservative such as paraben, an isotonizing agent such as sodium chloride, glucose, and glycerol, a buffer solution, a soothing agent, an adsorption preventing agent, a humectant, an antioxidant, a colorant, a sweetener, a flavor, and a fragrant substance. In this manner, the agent can be prepared as a sterilized aqueous solution, non-aqueous solution, suspension, liposome, emulsion, or the like. The injectable solution preferably has a physiological pH, preferably, a pH in the range of 6 to 8.

To form a semisolid preparation of the agent of the present invention, such as lotion, cream, or ointment, the phosphine transition metal complex is adequately mixed with fat, fatty oil, lanolin, petrolatum, paraffin, wax, plaster, resin, plastic, glycol, higher alcohol, glycerol, water, an emulsifier, a suspending agent, or the like.

The phosphine transition metal complex content in the anti-cancer agent of the present invention varies according to the form of administration, severity, and target dosage but is typically 0.001 to 80 percent by weight and preferably 0.1 to 50 percent by weight with respect to the total weight of the preparation.

The dosage of the anti-cancer agent of the present invention is appropriately determined by a doctor according to the age, sex, weight, symptom, and route of administration of the patient, for example. The dosage is usually in the range of 1 μg/kg to 1,000 mg/kg and preferably 10 μg/kg to 10 mg/kg daily for an adult in terms of amount of effective component. The agent may be administered once a day or in several divided doses (e.g., 2 to 4 doses). It should be noted that "amount of effective component" refers to the amount based on the phosphine transition metal complex content in the anti-cancer agent.

The anti-cancer agent of the present invention may be combined with a known chemical therapy, surgical therapy, radiation therapy, thermotherapy, or immune therapy.

EXAMPLES

The present invention will now be described by way of non-limiting examples below.

Example 1

Bis((R)-1-((S)-2-(dicyclohexylphosphino)ferrocenyl)ethyldicyclohexylphosphine)gold(I)chloride In a 25 mL two-neck flask purged with nitrogen gas, 0.10 g (0.17 mmol) of (R)-1-((S)-2-(dicyclohexylphosphino)ferrocenyl)ethyldicyclohexylphosphine (produced by Strem Chemicals Inc.,) and 3 mL of a degassed chloroform solution were charged. To the resulting mixture, 0.04 g (0.09 mmol) of tetrabutylammonium gold dichloride was added, and the resulting mixture was stirred at room temperature for 6 hours. The resulting solution was washed with water and the organic layer was exsiccated. The resulting brown solid was vacuum-dried to yield 0.11 g of bis((R)-1-((S)-2-(dicyclohexylphosphino)ferrocenyl)ethyldicyclohexylphosphine)gold(I)chloride (yield: 89%).

(Identification Data)
Mass(FAB, POS) m/z 1409. ($M^+$-$Cl^-$)

Example 2

Bis((R)-1-((S)-2-(diphenylphosphino)ferrocenyl)ethyldicyclohexylphosphine)gold(I)chloride In a 25 mL two-neck flask purged with nitrogen gas, 0.13 g (0.22 mmol) of (R)-1-((S)-2-(diphenylphosphino)ferrocenyl)ethyldicyclohexylphosphine (produced by Strem Chemicals Inc.,) and 3 mL of a degassed chloroform solution were charged. To the resulting mixture, 0.07 g (0.14 mmol) of tetrabutylammonium gold dichloride was added, and the resulting mixture was stirred at room temperature for 4 hours. The resulting solution was washed with water and the organic layer was exsiccated. The resulting brown solid was vacuum-dried to yield 0.15 g of bis((R)-1-((S)-2-(diphenylphosphino)ferrocenyl)ethyldicyclohexylphosphine)gold(I)chloride (yield: 98%).

(Identification Data)
Mass(FAB, POS) m/z 1385. ($M^+$-$Cl^-$)

Example 3

Bis((R)-1-((S)-2-(dicyclohexylphosphino)ferrocenyl)ethyldiphenylphosphine)gold(I)chloride In a 25 mL two-neck flask purged with nitrogen gas, 0.10 g (0.17 mmol) of (R)-1-((S)-2-(dicyclohexylphosphino)ferrocenyl)ethyldiphenylphosphine (produced by Strem Chemicals Inc.,) and 3 mL of a degassed chloroform solution were charged. To the resulting mixture, 0.06 g (0.12 mmol) of tetrabutylammonium gold dichloride was added, and the resulting mixture was stirred at room temperature for 24 hours. The resulting solution was washed with water and the organic layer was exsiccated. The resulting brown solid was vacuum-dried to yield 0.10 g of bis((R)-1-((S)-2-(dicyclohexylphosphino)ferrocenyl)ethyldiphenylphosphine)gold(I)chloride (yield: 83%).

(Identification Data)
Mass(FAB, POS) m/z 1385. ($M^+$-$Cl^-$)

Example 4

Bis((S)-1-((R)-2-(dicyclohexylphosphino)ferrocenyl)ethyldiphenylphosphine)gold(I)chloride In a 25 mL two-neck flask purged with nitrogen gas, 0.09 g (0.15 mmol) of (S)-1-((R)-2-(dicyclohexylphosphino)ferrocenyl)ethyldiphenylphosphine (produced by Strem Chemicals Inc.,) and 2 mL of a degassed chloroform solution were charged. To the resulting mixture, 0.05 g (0.08 mmol) of tetrabutylammonium gold dichloride was added, and the resulting mixture was stirred at room temperature for 24 hours. The resulting solution was washed with water and the organic layer was exsiccated. The resulting brown solid was vacuum-dried to yield 0.09 g of bis((S)-1-((R)-2-(dicyclohexylphosphino)ferrocenyl)ethyldiphenylphosphine)gold(I)chloride (yield: 84%).

(Identification Data)
Mass(FAB, POS) m/z 1385. ($M^+$-$Cl^-$)

The compounds obtained in Examples 1 to 4 are summarized in Table 1.
TABLE 1
| Structural formula |
|---|
| Example 1 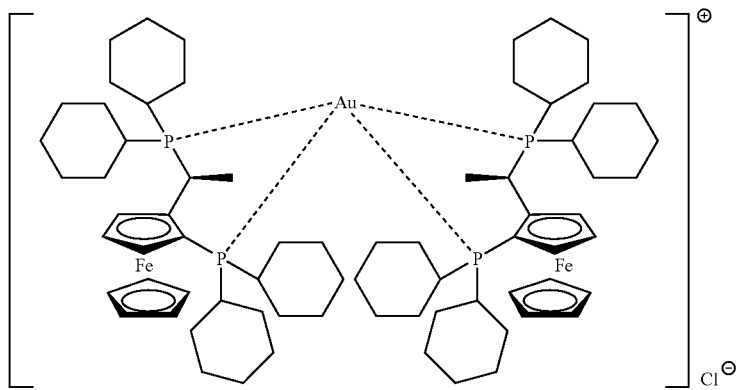 |
| Example 2 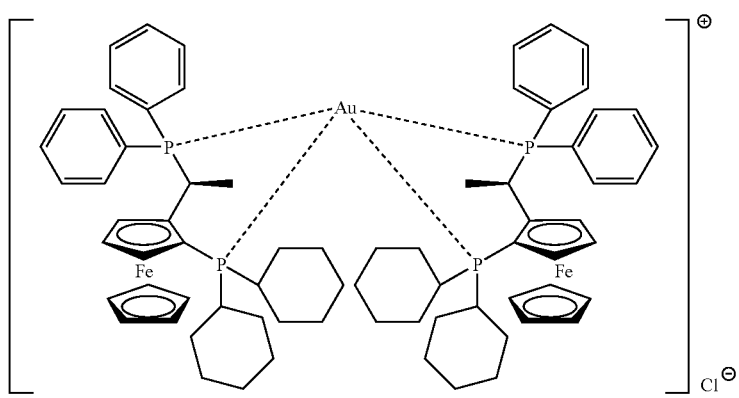 |
| Example 3 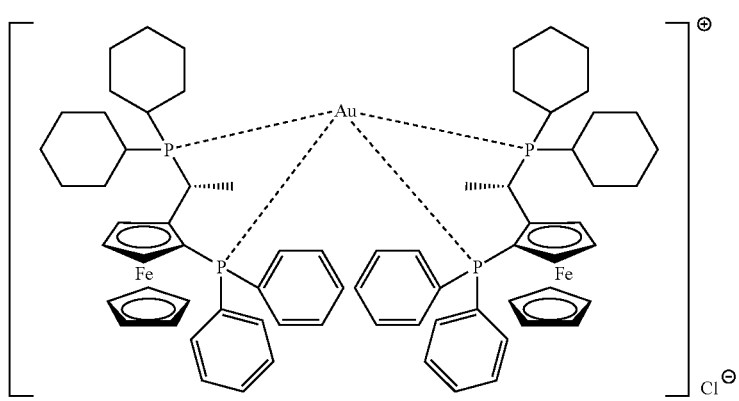 |

TABLE 1-continued

Structural formula

Example 4

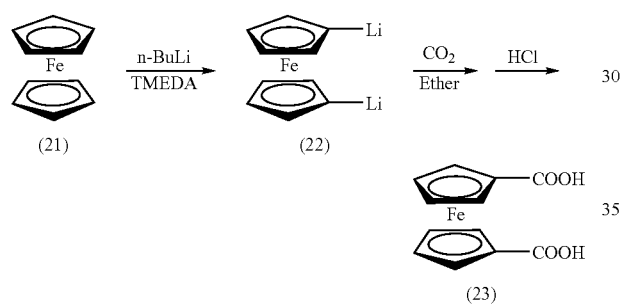

Synthetic Example 1

Preparation of 1,1-ferrocene dicarboxylic acid

Compound (23)

Under a nitrogen atmosphere, 53 mL (333.25 mmol) of tetramethylethylenediamine (TMEDA), 310 mL (537.75 mmol) of a solution of n-BuLi-hexane were mixed in a 1000 mL four-neck flask. To the flask, 20.01 g (107.55 mmol, compound (21)) of ferrocene dissolved in 400 mL of dry ether was injected by cannulation, followed by stirring at room temperature for 19 hours. A solution of dry ether with dry ice therein kept at −78° C. was added to the ferrocene-containing solution, and the resulting mixture was thoroughly stirred and left to stand for 3 hours. Water and hydrochloric acid were added to the resulting reaction solution to adjust the pH to 2. After recovery of precipitates generated, the solution was washed with water and ether and dried overnight in a desiccator to yield 27.30 g of 1,1'-ferrocene dicarboxylic acid (compound 23)) as a red-brown solid (yield: 93%).

Preparation of 1,1-ferrocene di(carboxylic acid chloride)

Compound (17)

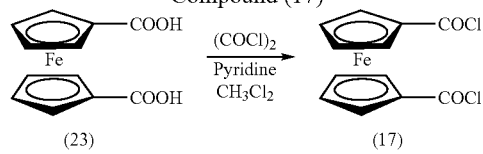

In a nitrogen atmosphere, 27.92 g (28.09 mmol) of 1,1'-ferrocene dicarboxylic acid (compound (23)) prepared as above was placed in a 500 mL four-neck flask. To the flask, 115 mL of methylene chloride and 0.12 mL of pyridine were added, and 16.83 mL (175.86 mmol) of oxalyl chloride was added dropwise over 1 hour, followed by refluxing for 16 hours. The solvent was distilled away and extraction was conducted under a nitrogen atmosphere with a hexane-ethylene chloride (1:1) mixed solvent to extract 6.29 g of a red solid of 1,1'-ferrocene di(carboxylic acid chloride) (compound (17)) (yield: 70%).

Example 5

Preparation of 1,1-bis[(S)—N-(1-substituted-2-hydroxyethyl)amide]ferrocene

Compound (19)

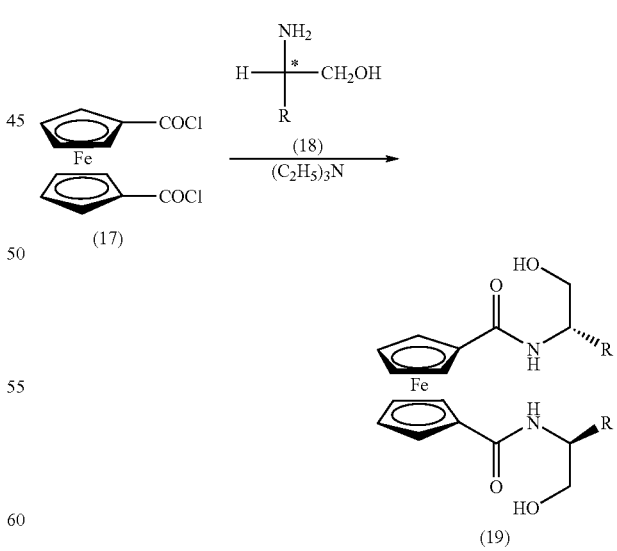

Under a nitrogen atmosphere, in a 100 mL two-neck flask, 2.09 g (20.28 mmol) of an amino alcohol compound represented by general formula (18) where R represents an isopropyl group was dissolved in 5.2 mL (36.87 mmol) of triethyl amine and 65 mL of methylene chloride to prepare solution A. In 115 mL of methylene chloride, 2.87 g (9.22 mmol) of 1,1'-ferrocene di(carboxylic acid chloride) prepared in Synthetic Example 1 was dissolved to prepare solution B.

Solution B was slowly added to solution A dropwise over 2 hours, followed by stirring for 24 hours to conduct reaction. Upon completion of reaction, the reaction solution was washed with water and saturated saline and dried over anhydrous sodium sulfate. The solvent was then distilled away to obtain 3.80 g of 1,1'-bis[(S)—N-(1-substituted-2-hydroxyethyl)amide]ferrocene represented by general formula (19) above where R is an isopropyl group as a brown solid (yield: 93%).

(Identification Data)

$^1$H-NMR (CDCl$_3$, 400 M): 6.34 (d, j=8.5 Hz, 2H, NH), 4.76 (brs, 2H, FcH), 4.50 (brs, 2H, FcH), 4.47 (brs, 2H, FcH), 4.38 (brs, 2H, FcH), 3.93 (m, 2H, NCH), 3.88 (dd, J=3.0, 11.6 Hz, 2H, OCH), 3.75 (dd, J=6.0, 11.6 Hz, 2H, OCH), 1.96 (m, 2H, Me$_2$CH), 1.02 (d, j=6.6 Hz, 6H, CH$_3$), 1.00 (d, J=6.9 Hz, 6H, CH$_3$)

Preparation of 1,1'-bis[(S)-4-substituted oxazolin-2-yl]ferrocene

Compound (20)

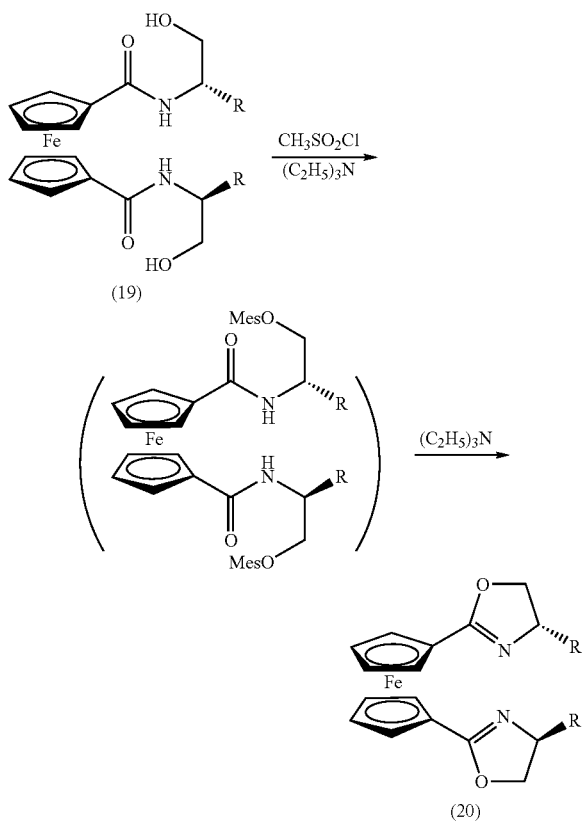

Under a nitrogen atmosphere, in a 500 mL round-bottomed flask, 3.80 g (8.55 mmol) of 1,1-bis[(S)—N-(1-substituted-2-hydroxyethyl)amide]ferrocene represented by general formula (19) where R is an isopropyl group and prepared as above was dissolved in 43 mL of methylene chloride and 86.34 mL (44.46 mmol) of triethylamine. To the resulting mixture, a mixed solvent of 1.78 mL (22.23 mmol) of methanesulfonyl chloride an 5.5 mL of methylene chloride was gradually added dropwise while cooling, and the reaction was conducted for 16 hours under stirring. Subsequently, the mixture was washed with water, iced water, and saturated saline and dried over anhydrous sodium sulfate. The solvent was distilled away and the residue was subjected to isolation purification by silica gel chromatography to obtain 2.96 g of 1,1'-bis[(S)-4-substituted oxazolin-2-yl]ferrocene represented by general formula (20) where R is an isopropyl group as a brown solid (yield: 85%).

(Identification Data)

$^1$H-NMR (CDCl$_3$, 400 M): 4.77 (brs, 2H, FcH), 4.74 (brs, 2H, FcH), 4.35 (brs, 4H, FcH), 4.31 (dd, J=7.9, 10.1 Hz, 2H, OCH), 4.06 (t, J=7.9 Hz, 2H, OCH), 3.98 (m, 2H, NCH), 1.86 (m, 2H, Me$_2$CH), 1.02 (d, J=6.7 Hz, 6H, CH$_3$), 0.94 (d, J=6.6 Hz, 6H, CH$_3$)

Preparation of 1,1'-bis(diphenylphosphino)-2,2-bis-[(S)-4-substituted oxazolin-2-yl]ferrocene Compound (2d))

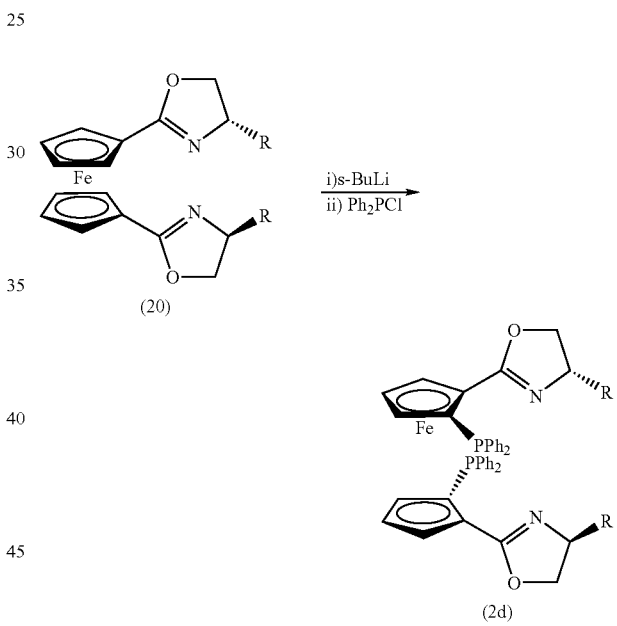

Under an argon atmosphere, in a 100 mL round-bottomed flask, 2.81 g (6.87 mmol) of 1,1'-bis[(S)-4-substituted oxazolin-2-yl]ferrocene represented by general formula (20) where R is an isopropyl group and prepared as above was completely dissolved in 45 mL of dry THF. To this solution, 3.02 mL (19.28 mmol) of N,N,N',N'-tetramethylethylenediamine (TMEDA) was added. The resulting mixture was placed in an acetone-dry ice bath to maintain a temperature of −78° C. during which 15.51 mL (19.28 mmol) of a sec-BuLi-hexane solution was gradually injected to this mixture, followed by stirring for 4 hours. Subsequently, the acetone-dry ice bath was changed to an ice bath. The resulting mixture was left therein for 15 minutes, and 3.02 mL (19.28 mmol) of diphenylphosphine chloride was added thereto. After stirring overnight, the solution was distilled. The residue was subjected to isolation purification under an argon atmosphere by silica gel chromatography to obtain 1.50 g of a brown solid of 1,1'-bis(diphenylphosphino)-2,2-bis-[(S)]-4-substituted oxazolin-2- yl]ferrocene represented by general formula (2d) above where R is an isopropyl group (yield: 27%).

(Identification Data)

$^1$H-NMR (CDCl$_3$, 400 M):

7.30 (dd, J=7.9, 16.2 Hz, 8H, ArH), 7.22 (m, 8H, PhH), 7.16 (m, 4H, PhH), 5.05 (brs, 2H, FcH), 4.55 (brs, 2H, FcH), 4.28 (dd, J=8.2, 9.7 Hz, 2H, OCH), 3.87 (m, 2H, NCH), 3.65 (t, j=9.2 Hz, 2H, OCH), 3.48 (brs, 2H, FcH), 1.67 (m, 2H, Me$_2$CH), 0.82 (d, J=6.8 Hz, 6H, CH$_3$), 0.62 (d, J=6.8 Hz, 6H, CH$_3$)

$^{13}$C-NMR (CDCl$_3$, δ0% H$_3$PO$_4$, 400 M); 163.94, 163.9, 138.9, 138.8, 137.5, 137.3, 134.6 (2C), 134.2 (2C), 132.5 (2C), 132.3 (2C), 128.9 (2C), 128.2 (2C), 128.1 (2C), 128.05 (2C), 128.0 (2C), 127.9 (2C), 80.3, 80.0, 77.5, 77.3, 75.9, 75.1, 75.01, 74.98, 72.0 (2C), 69.5, 31.8, 18.7, 17.3 (2C)

$^{31}$P-NMR (CDCl$_3$, 85% H$_3$PO$_4$, 400 M); –16.81

IR (KBr, cm$^{-1}$)

3051.3, 1956.4, 1585.8, 1474.0, 1434.9, 1354.3, 1269.2, 1061.9, 1030.7, 876.7, 829.7, 635.7

HRMS; calcd for C$_{46}$H$_{46}$FeN$_2$O$_2$P$_2$, 777.2384, found: 777.2410 m.p.: 75-75° C.

[α]$^{20}$D=–136.6 (c=0.80, CHCl$_3$)

Synthesis of bis(1,1'-bis-(diphenylphosphino)-2,2-bis-[(S)-4-isopropyl-2-yl]ferrocene)digold(I)dichloride In a 100 mL two-neck flask purged with nitrogen gas, a degassed THF solution of 0.78 g (1.0 mmol) of 1,1'-bis(diphenylphosphino)-2,2-bis-[(S)-4-isopropyl-2-yl]ferrocene represented by general formula (2d) where R is an isopropyl group and prepared as above was charged. To this solution, 0.51 g (1.0 mmol) of tetrabutylammonium gold dichloride was added, and the resulting mixture was stirred at room temperature for 24 hours. The resulting mixture was exsiccated and dissolved in ethyl acetate. The resulting solution was washed with water and the organic layer was exsiccated. The resultant brown solid was vacuum-dried to obtain 0.89 g of bis(1,1'-bis-(diphenylphosphino)-2,2-bis-[(S)-4-isopropyl-2-yl]ferrocene)digold(I)dichloride (yield: 88%).

(Identification Data)

Mass (ESI, POS) m/z 1982. (M$^+$-Cl$^-$)

Example 6

Synthesis of bis(1,1'-bis-(diphenylphosphino)-2,2-bis-[(S)-4-tert-butyl-2-yl]ferrocene)digold(I)dichloride Reaction was conducted under the same conditions as those of Example 5 except that an amino alcohol compound represented by general formula (18) where R was a tert-butyl group was used. As a result, 1.04 g of bis(1,1'-bis-(diphenylphosphino)-2,2-bis-[(S)-4-tert-butyl-2-yl]ferrocene)digold(I)dichloride was obtained (yield: 99%).

(Identification Data)

Mass (ESI, POS) m/z 2038. (M$^+$-Cl$^-$)

Example 7

Synthesis of bis(1,1'-bis-(diphenylphosphino)-2,2-bis-[(S)-4-isobutyl-2-yl]ferrocene)digold(I)dichloride Reaction was conducted under the same conditions as those of Example 5 except that an amino alcohol compound represented by general formula (18) where R was an isobutyl group was used. As a result, 0.92 g of bis(1,1'-bis-(diphenylphosphino)-2,2-bis-[(S)-4-isobutyl-2-yl]ferrocene)digold(I)dichloride was obtained (yield: 89%).

(Identification Data)

Mass (ESI, POS) m/z 2038. (M$^+$-Cl$^-$)

Example 8

Synthesis of bis(1,1'-bis-(diphenylphosphino)-2,2-bis-[(S)-4-sec-butyl-2-yl]ferrocene)digold(I)dichloride Reaction was conducted under the same conditions as those of Example 5 except that an amino alcohol compound represented by general formula (18) where R was a sec-butyl group was used. As a result, 0.81 g of bis(1,1'-bis-(diphenylphosphino)-2,2-bis-[(S)-4-sec-butyl-2-yl]ferrocene)digold(I)dichloride was obtained (yield: 89%).

(Identification Data)

Mass (ESI, POS) m/z 2038. (M$^+$-Cl$^-$)

Example 9

Synthesis of 1,1'-bis-(diphenylphosphino)-2,2-bis-[(S)-2-isopropyl-2-acetylaminoethyl ester]ferrocene Compound (2f-1)

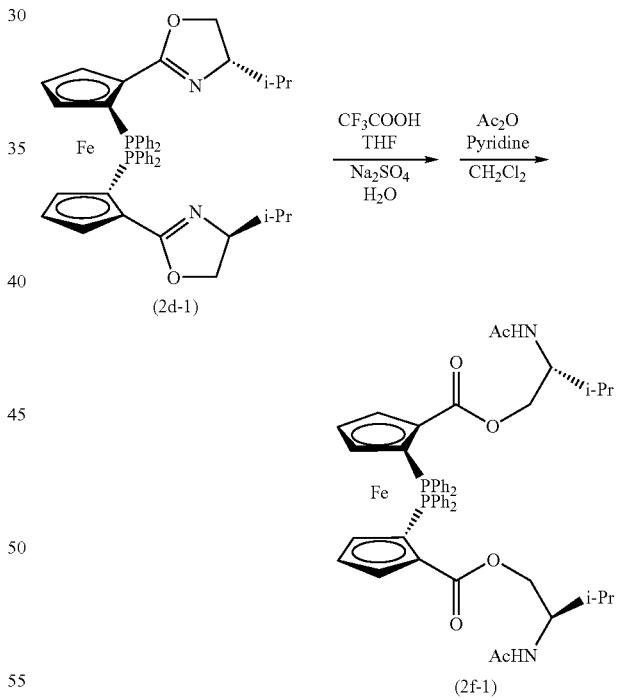

Under a nitrogen atmosphere, in a 100 mL round-bottomed flask, 1.55 g (2.0 mmol) of 1,1'-bis-(diphenylphosphino)-2,2-bis-[(S)-4-substituted oxazolin-2-yl]ferrocene represented by general formula (2d-1) and prepared as in Example 5 was completely dissolved in 40 mL of THF. To the resulting solution, 18.80 g (132.38 mmol) of anhydrous sodium sulfate was added, and then 2.0 mL (111.11 mmol) of water was added under stirring. The resulting mixture was cooled in an ice bath, and 3.8 mL (50.0 mmol) of trifluoroacetic acid was gradually added thereto dropwise. The resulting mixture was stirred overnight under a nitrogen atmosphere, and then filtered to remove anhydrous sodium sulfate. The solvent was distilled away, the residue was dissolved in 30 mL of methylene chloride, and 7.2 mL of pyridine was added to the resulting solution. While ice-cooling the resulting mixture, 12 mL (76.0 mmol) of acetic anhydride was added thereto, followed by stirring under a nitrogen atmosphere overnight. The mixture was then washed with HCl, water, and saturated saline, dried over anhydrous magnesium sulfate, and distilled to remove the solvent. The residue was subjected to isolation purification by silica gel chromatography to obtain 1.32 g of 1,1'-bis-(diphenylphosphino)-2,2-bis-[(S)-2-isopropyl-2-acetylaminoethyl ester]ferrocene (compound (2f-1) as a red-brown solid (yield: 73.7%).

(Identification Data)

$^1$H-NMR (CDCl$_3$, 400 M):

7.29 (m, 8H, PhH), 7.22 (m, 8H, PhH), 7.12 (m, 4H, PhH), 6.59 (d, J=8.8 Hz, 2H, NH), 5.06 (brs, 2H, FcH), 4.66 (brs, 2H, FcH), 4.41 (dd, J=2.6, 11.5 Hz, 2H, OCH), 4.13 (m, 2H, NCH), 3.95 (dd, J=7.2, 11.5 Hz, 2H, OCH), 3.45 (brs, 2H, FcH), 2.08 (m, 2H, Me$_2$CH), 1.88 (s, 6H, COCH$_3$), 1.07 (d, J=6.5 Hz, 6H, CH$_3$), 1.02 (d, J=6.5 Hz, 6H, CH$_3$)

$^{13}$C-NMR (CDCl$_3$, 80%, 100 M);

170.4, 170.3, 138.6, 138.4, 136.6, 136.5, 135.0, 134.8, 132.2, 132.0, 130.0, 128.7, 128.6, 128.5, 66.0, 53.4, 29.6, 23.4, 20.0, 19.9

$^{31}$P-NMR (CDCl$_3$, 85% H$_3$PO$_4$, 400 M): −17.370

Synthesis of bis(1,1-bis-(diphenylphosphino)-2,2-bis-[(S)-2-isopropyl-2-acetylaminoethyl ester]ferrocene)gold(I)chloride In a 25 mL two-neck flask purged with nitrogen gas, a degassed THF solution of 0.90 g (1.0 mmol) of 1,1'-bis-(diphenylphosphino)-2,2-bis-[(S)-2-isopropyl-2-acetylaminoethyl ester]ferrocene (compound (2f-1) prepared as above was charged. To the solution, 0.31 g (0.6 mmol) of tetrabutylammonium gold dichloride was added, followed by stirring at room temperature for 2 hours. To the resulting solution, diethyl ether was added, and the solid precipitates were filtered. The resulting brown solids were vacuum-dried to obtain 0.96 g of bis(1,1'-bis-(diphenylphosphino)-2,2-bis-[(S)-2-isopropyl-2-acetylaminoethyl ester]ferrocene)gold(I) chloride (yield: 96%).

(Identification Data)

Mass (ESI, POS) m/z 1990. (M$^+$-Cl$^-$)

Example 10

Synthesis of (−)-(S)—(S)-1,1'-bis-(diphenylphosphino)-2,2'-bis(methoxycarbonyl)ferrocene Compound (2h-2)

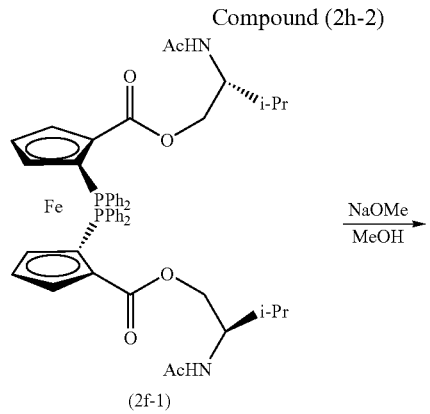

(2f-1)

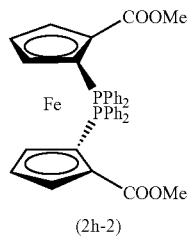

(2h-2)

Under a nitrogen atmosphere, in a 500 mL round-bottomed flask, 5.0 g (5.58 mmol) of 1,1'-bis-(diphenylphosphino)-2,2-bis-[(S)-2-isopropyl-2-acetylaminoethyl ester]ferrocene (compound (2f-1)) was completely dissolved in 50 mL of THF. Under a nitrogen atmosphere, sodium methoxide prepared by adding 5.10 g (221.74 mmol) of metallic sodium to 170 mL of methanol was injected to the flask, followed by stirring for 24 hours. The mixture was neutralized with a acetic acid-methanol solution, washed with water and saturated saline, dried over anhydrous magnesium sulfate, and subjected to distillation to remove the solvent. The mixture was then subjected to isolation purification by silica gel column chromatography to obtain 2.61 g of (−)-(S)—(S)-1,1'-bis(diphenylphosphino)-2,2'-bis(methoxycarbonyl)ferrocene (compound (2h-2)) as an orange solid. (yield: 69.8%).

[Identification Data]

$^1$H-NMR (CDCl$_3$, 400 M):

7.31-7.14 (m, 20H, PhH), 5.09 (brs, 2H, FcH), 4.60 (brs, 2H, FcH), 3.74 (s, 6H, CH$_3$), 3.49 (brs, 2H, FcH)

$^{13}$C-NMR (CDCl$_3$, 100 M);

170.3, 139.0, 138.8, 137.7, 137.6, 135.0, 134.8, 132.6, 132.6, 132.4, 129.5, 128.5, 128.5, 52.0

Synthesis of ((−)-(S)—(S)-1,1'-bis(diphenylphosphino)-2,2'-bis(methoxycarbonyl)ferrocene)gold(I) chloride In degassed THF in a 25 mL two-neck flask purged with nitrogen gas, 0.80 g (1.2 mmol) of (−)-(S)—(S)-1,1'-bis-(diphenylphosphino)-2,2'-bis-(methoxycarbonyl)ferrocene (compound (2h-2)) prepared as above was added. To this mixture, 0.37 g (0.7 mmol) of tetrabutylammonium gold dichloride was added, and the mixture was stirred at room temperature for 2 hours. The resulting solution was exsiccated and dissolved in ethyl acetate. The resulting solution was washed with water and the organic layer was exsiccated. The resultant brown solid was vacuum-dried to obtain 0.78 g of ((−)-(S)—(S)-1,1'-bis(diphenylphosphino)-2,2'-bis(methoxycarbonyl)ferrocene)gold(I)chloride (yield: 83%).

Identification Data

Mass (ESI, POS) m/z 1537. (M$^+$-Cl$^-$)

Example 11

Synthesis of (−)-(S)—(S)-1,1'-bis(diphenylphosphino)-2,2'-bis(ethoxycarbonyl)ferrocene Compound (2h-3)

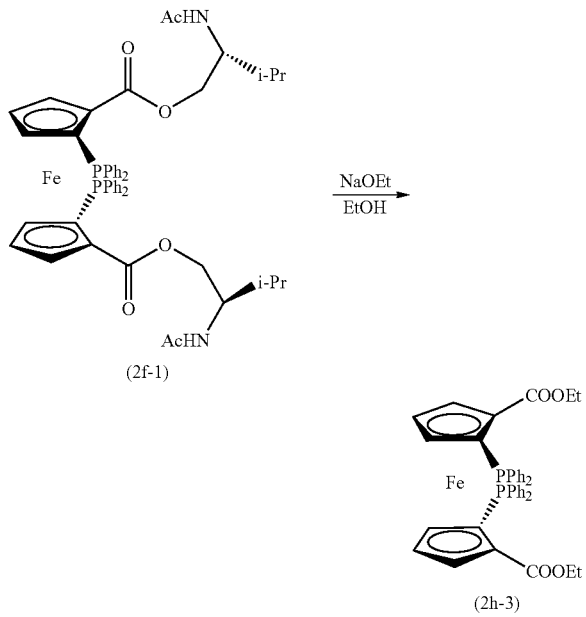

Under a nitrogen atmosphere, 5.50 g (6.13 mmol) of 1,1'-bis-(diphenylphosphino)-2,2-bis-[(S)-2-isopropyl-2-acetylaminoethyl ester]ferrocene (compound (2f-1)) prepared as in Example 9 was completely dissolved in 50 mL of THF in a 200 mL round-bottomed flask. To this solution, sodium ethoxide prepared by adding 6.0 g (260.87 mmol) of metallic sodium to 170 mL of ethanol under a nitrogen atmosphere was injected, followed by stirring for 48 hours. The resulting mixture was neutralized with an acetic acid-methanol solution, washed with water and saturated saline, dried over anhydrous magnesium sulfate, and subjected to distillation to remove the solvent. Isolation purification was then conducted by silica gel column chromatography to yield 2.60 g of (−)-(S)—(S)-1,1'-bis(diphenylphosphino)-2,2'-bis(ethoxycarbonyl)ferrocene (compound (2h-3)) as an orange solid (yield: 60.7%).

(Identification Data)
$^1$H-NMR (CDCl$_3$, 400 M)
7.31-7.12 (m, 20H, PhH), 5.08 (brs, 2H, FcH), 4.67 (brs, 2H, FcH), 4.33-4.11 (m, 4H, CH$_2$), 3.46 (brs, 2H, FcH), 1.20 (t, 6H, CH$_3$)
$^{13}$C-NMR (CDCl$_3$, 100 M);
170.0, 139.0, 138.90, 137.7, 137.5, 135.0, 134.7, 132.6, 132.4, 129.5, 128.5, 128.4, 60.9, 14.5
$^{31}$P-NMR (CDCl$_3$, 85% H$_3$PO$_4$, 400 M): −17.607

Synthesis of bis((−)-(S)—(S)-1,1'-bis(diphenylphosphino)-2,2-bis(ethoxycarbonyl)ferrocene)gold(I) chloride In a 25 mL two-neck flask purged with nitrogen gas, 0.84 g (1.2 mmol) of (−)-(S)—(S)-1,1'-bis-(diphenylphosphino)-2,2'-bis(ethoxycarbonyl)ferrocene (compound (2h-3)) prepared as above was added to a degassed chloroform solution. To the solution, 0.37 g (0.6 mmol) of tetrabutylammonium gold dichloride was added, followed by stirring at room temperature for 3 hours. The resulting solution was exsiccated and dissolved in ethyl acetate. The solution was washed with water and the organic layer was exsiccated. The resulting brown solid was vacuum-dried to obtain 0.96 g of bis((−)-(S)—(S)-1,1'-bis-(diphenylphosphino)-2,2'-bis(ethoxycarbonyl)ferrocene)gold(I)chloride (yield: 98%).

(Identification Data)
Mass (ESI, POS) m/z 1593. (M$^+$-Cl$^-$)

The structural formulae of the phosphine transition metal complexes obtained in Examples 5 to 11 are summarized in Tables 2 and 3.

TABLE 2

Structural formula

| Example 5 | 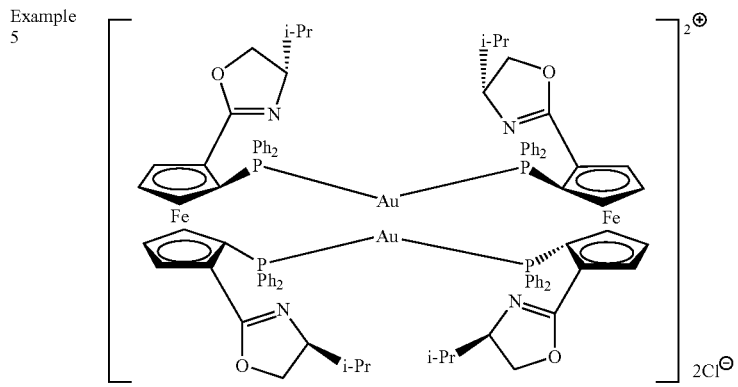 |
|---|---|

TABLE 2-continued
| Structural formula |
|---|
Example 6
Example 7
Example 8
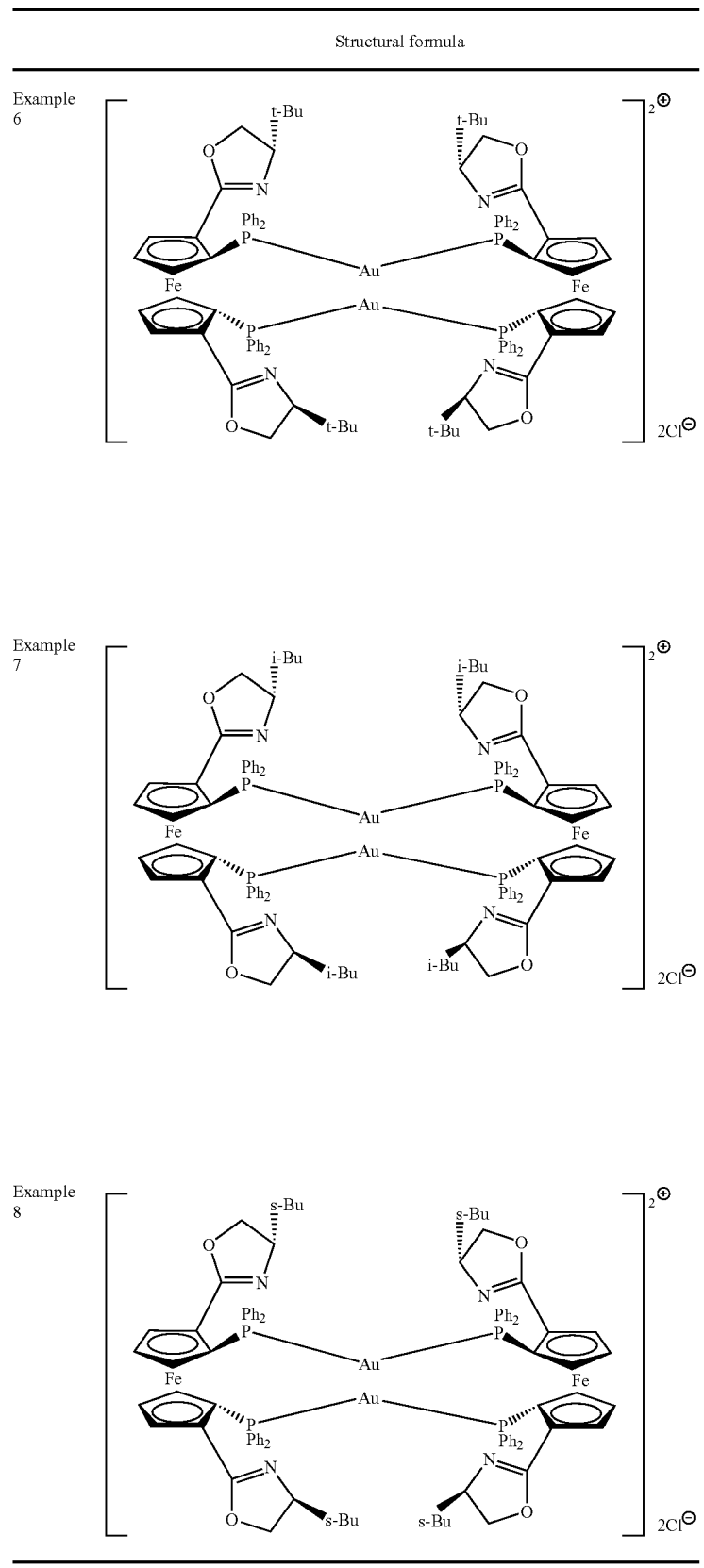

TABLE 3

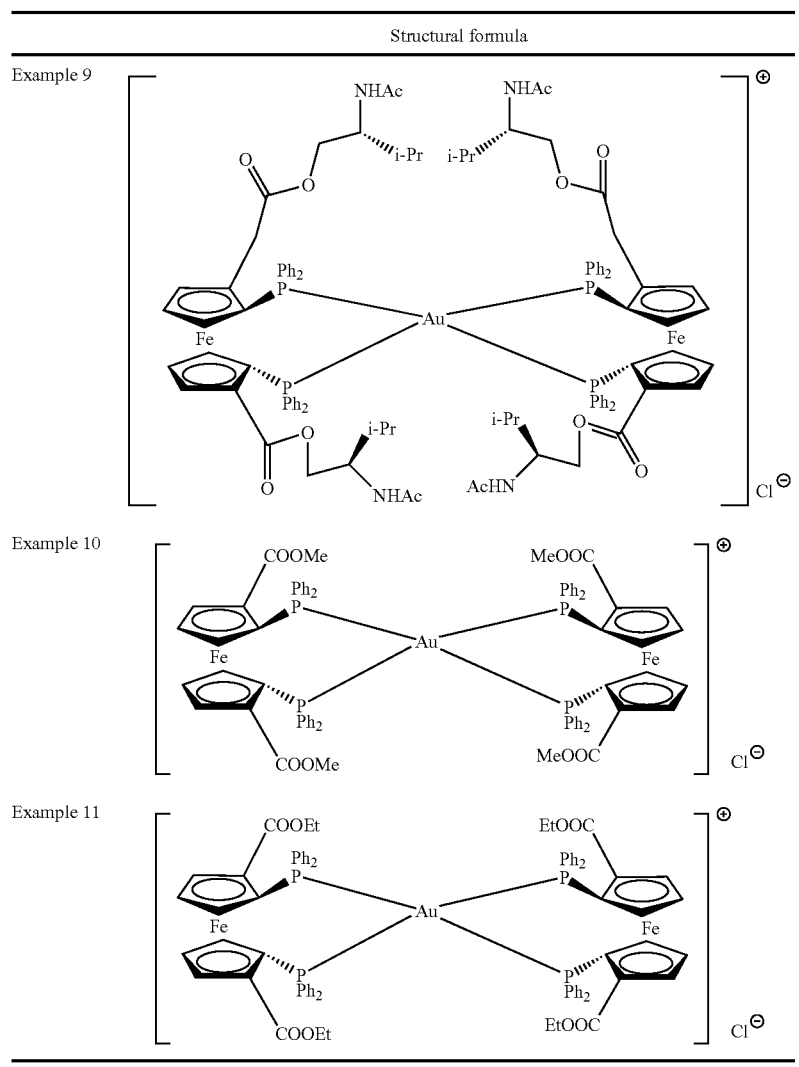

| | Structural formula |
|---|---|
| Example 9 | |
| Example 10 | |
| Example 11 | |

<Evaluation of Anti-Cancer Activity>

The activity of the phosphine-gold complex having a ferrocene skeleton obtained in each of Examples 1 to 9 against tumor cells was evaluated as follows. For comparison, the same test was conducted on cisplatin (Comparative Example 1).

HL-60 (human acute myeloid leukemia cells) as the cancerous cells was cultured under a 5% $CO_2$ atmosphere in a wet incubator at 37° C. in a Roswell Park Memorial Institute medium (RPMI 1640) supplemented with 10% fetal bovine serum and 1% antibiotic and antimycotic.

The cells were washed with PBS and counted. A $1\times10^6$ cells/mL suspension was then prepared using the same medium. The suspension was added to a sterilized 96-well microplate at a density of 50000 cells per well.

Each of the phosphine-gold complexes prepared in Example 1 to 8 completely dissolved in water or dimethyl sulfoxide and a cisplatin solution (Comparative Example 1) was added, and the culture was continued for 24 hours in the incubator.

The number of survived cells was then evaluated by a modified Mosmann method (T. Mosmann, J. Immunol. Method (1983) 65, 55-63). That is, a solution of a tetrazolium salt (3,[4,5-dimethylthiazol-2-yl]-2,5-diphenyltetrazolium bromide (MTT)) was added, and the culture was continued for 3 hours under the same conditions. Formazan crystals generated by enzymatic activity of the mitochondria in the cells were dissolved in 0.04 mol HCl/isopropyl alcohol and the absorbance at 595 nm was measured using a microplate reader (Bio-Rad 550). In order to eliminate the background, the absorbance at 630 nm was measured and subtracted from the observed absorbance at 595 nm. The resulting number was evaluated as the number of surviving cells and the concentration of inhibitor that inhibits cell growth to 50% ($IC_{50}$) was calculated. Note that in calculating the $IC_{50}$ value, the average of values of at least three experiments conducted under the same conditions was used. The results are shown in Table 4.

TABLE 4

| | $IC_{50}$ (µM/L) |
|---|---|
| Example 1 | 19.2 |
| Example 2 | 8.69 |
| Example 3 | 7.92 |
| Example 4 | 9.21 |
| Example 5 | 0.803 |
| Example 6 | 2.31 |

TABLE 4-continued

|  | IC$_{50}$ (μM/L) |
|---|---|
| Example 7 | 2.1 |
| Example 8 | 3.54 |
| Comparative Example 1 | 23.6 |

As apparent from the results shown in Table 4, the phosphine transition metal complex having the ferrocene skeleton according to the present invention has an anti-cancerous activity superior to that of cisplatin.

Example 12

Production of Powdered Drug

For each of the phosphine-gold complexes obtained as in Examples 1 to 11, a powdered drug was made by mixing 50 g of the complex with 400 g of lactose and 50 g of cornstarch using a blender.

Example 13

Production of Granular Drug

For each of the phosphine-gold complexes obtained as in Examples 1 to 11, a granular drug was made by mixing 50 g of the complex with 250 g of lactose and 50 g of low-substituted hydroxypropylcellulose, kneading the resulting mixture with 150 g of a 10% aqueous hydroxypropylcellulose solution, granulating the resulting mixture with a pellet mill, and drying the resulting pellets.

Example 14

Production of Tablet Drug

For each of the phosphine-gold complexes obtained as in Examples 1 to 11, a tablet drug was prepared by mixing 50 g of the complex with 250 g of lactose, 120 g of cornstarch, 75 g of crystalline cellulose, and 5 g of magnesium stearate by using a blender and then tabletting the mixture using a tablet machine.

Example 15

Production of Capsule Drug

For each of the phosphine-gold complexes obtained as in Examples 1 to 11, a capsule drug was prepared by mixing 25 g of the complex with 300 g of lactose, 170 g of cornstarch, and 5 g of magnesium stearate by using a V-type mixer and placing the resultant mixture into No. 3 capsules 180 mg each Example 16

Production of Injectable Solution

For each of the phosphine-gold complexes obtained as in Examples 1 to 11, an injectable solution was prepared by dissolving 100 mg of the complex and 100 mg of glucose in 2 mL of purified water, filtering the resulting solution, dispensing the filtrate in a 2 mL ampoule, and sealing and sterilizing the ampoule.

Example 17

Production of Lotion Drug

For each of the phosphine-gold complexes obtained as in Examples 1 to 11, a lotion drug was prepared by mixing and dissolving 1 g of the complex, 3 g of ethanol, 0.2 g of hydroxyethylcellulose, and 0.1 g of methyl parahydroxybenzoate in 100 mL of purified water.

Example 18

Production of Ointment Drug

For each of the phosphine-gold complexes obtained as in Examples 1 to 11, an ointment drug was prepared by melting and dispersing 2 g of the complex, 6 g of liquid paraffin, 2 g of beeswax, 3 g of self-emulsifying-type glyceryl monostearate, and 5 g of white petrolatum under heating.

Example 19

Production of Cream Drug

For each of the phosphine-gold complexes obtained as in Examples 1 to 11, a cream drug was prepared by dispersing 2 g of the complex in 2 g of glyceryl monostearate, 4 g of stearyl alcohol, 2 g of octyldodecanol, and 5 g of polyoxyethylene-sorbitan monooleate under heating, adding thereto 0.1 g of methyl parahydroxybenzoate dissolved in 5 g of glycerol and 60 g of purified water under heating, emulsifying the resulting mixture by high-speed stirring, and cooling the resulting emulsion.

The phosphine transition metal complex having the ferrocene skeleton according to the present invention has an anti-cancer activity and can be used as an anti-cancer agent.

What is claimed is:

1. A phosphine transition metal complex having a ferrocene skeleton, the complex comprising:
   at least two phosphine derivatives represented by general formula (1) or general formula (2) as ligands; and
   a transition metal atom selected from the group consisting of gold, copper, platinum, and silver:

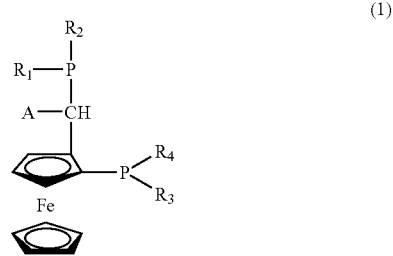

(1)

(wherein $R_1$, $R_2$, $R_3$, and $R_4$ each represent a linear or branched alkyl group, a cycloalkyl group, an alkoxy group, an aryl group, or an aralkyl group; and A represents a linear or branched alkyl group, a phenyl group, or a hydrogen atom),

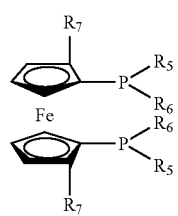

(2)

(wherein R$_5$ and R$_6$ each represent a linear or branched alkyl group, a cycloalkyl group, an alkoxy group, an aryl group, or an aralkyl group, and R$_7$ represents a monovalent organic group).

2. The phosphine transition metal complex according to claim 1, wherein the phosphine transition metal complex having the ferrocene skeleton is represented by general formula (3)

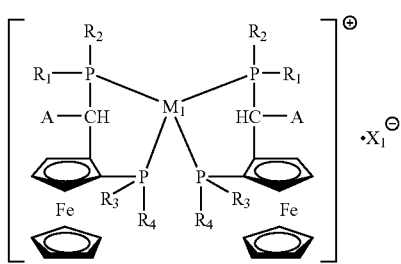

(3)

(wherein R$_1$, R$_2$, R$_3$, R$_4$, and A are the same as above, M$_1$ represents a transition metal atom selected from the group consisting of gold, copper, platinum, and silver, and X$_1$ represents an anion).

3. The phosphine transition metal complex according to claim 1, wherein the phosphine transition metal complex having the ferrocene skeleton is represented by general formula (4)

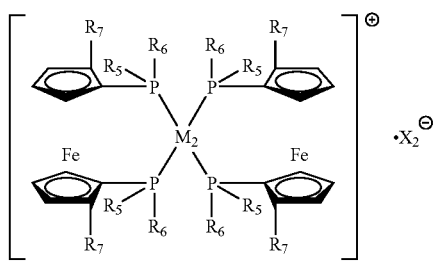

(4)

(wherein R$_5$, R$_6$, and R$_7$ are the same as above, M$_2$ represents a transition metal atom selected from the group consisting of gold, copper, platinum, and silver, and X$_2$ represents an anion).

4. The phosphine transition metal complex according to claim 1, wherein the phosphine transition metal complex having the ferrocene skeleton is represented by general formula (5)

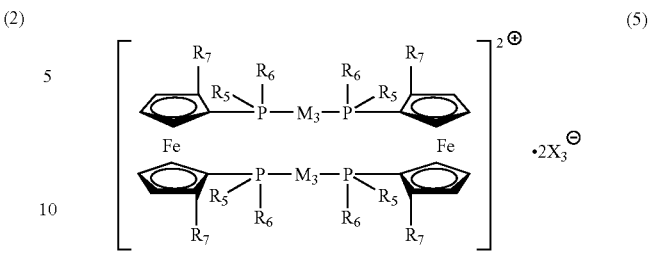

(5)

(wherein R$_5$, R$_6$, and R$_7$ are the same as above, M$_3$ represents a transition metal atom selected from the group consisting of gold, copper, platinum, and silver, and X$_3$ represents an anion).

5. The phosphine transition metal complex according to claim 1, wherein R$_1$, R$_2$, R$_3$, and R$_4$ in general formula (3) each represent a group selected from the group consisting of a phenyl group and a cycloalkyl group.

6. The phosphine transition metal complex according to claim 1, wherein R$_7$ in general formula (4) represents a group selected from the group consisting of a linear or branched C$_1$-C$_5$ alkyl group, a carboxyl group, and a carboxylic ester group.

7. The phosphine transition metal complex having the ferrocene skeleton according to claim 1, wherein R$_7$ in general formula (5) represents a substituted or unsubstituted oxazoline group.

8. The phosphine transition metal complex according to claim 1, wherein M$_1$, M$_2$, or M$_3$ is a gold atom.

9. A process for making the phosphine transition metal complex having the ferrocene skeleton according to claim 1, comprising reacting a phosphine derivative represented by general formula (1) or (2) with a transition metal salt of gold, copper, platinum, or silver:

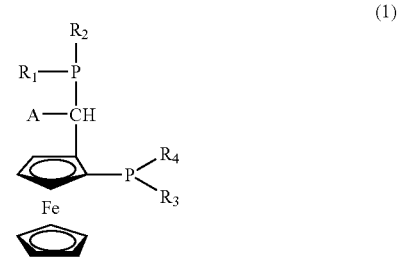

(1)

(wherein R$_1$, R$_2$, R$_3$, and R$_4$ each represent a linear or branched alkyl group, a cycloalkyl group, an alkoxy group, an aryl group, or an aralkyl group; and A represents a linear or branched alkyl group, a phenyl group, or a hydrogen atom),

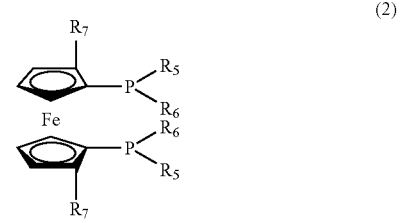

(2)

(wherein $R_5$ and $R_6$ each represent a linear or branched alkyl group, a cycloalkyl group, an alkoxy group, an aryl group, or an aralkyl group, and $R_7$ represents a monovalent organic group).

10. An anti-cancer agent comprising the phosphine transition metal complex having the ferrocene skeleton according to any one of claims 1 to 8.

* * * * *